United States Patent
Warman et al.

(10) Patent No.: US 7,127,292 B2
(45) Date of Patent: Oct. 24, 2006

(54) ADDRESSING RECURRENT ATRIAL FIBRILLATION

(75) Inventors: Eduardo N. Warman, Maple Grove, MN (US); Stefan Holzer, Vienna (AT); Helmut Puererfellner, Engerwitzdorf (AT); Douglas A. Hettrick, Blaine, MN (US); Paul D. Ziegler, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 636 days.

(21) Appl. No.: 10/284,873

(22) Filed: Oct. 31, 2002

(65) Prior Publication Data

US 2004/0088010 A1    May 6, 2004

(51) Int. Cl.
*A61N 1/36* (2006.01)
*A61N 1/365* (2006.01)

(52) U.S. Cl. .............................. 607/25; 607/4; 607/14; 607/17

(58) Field of Classification Search .................. 607/4, 607/14, 17, 25
See application file for complete search history.

(56) References Cited

U.S. PATENT DOCUMENTS

| 5,193,536 A | 3/1993 | Mehra .................... 128/419 D |
| 5,330,513 A | 7/1994 | Nichols et al. ............... 607/32 |
| 5,713,929 A | 2/1998 | Hess et al. .................... 607/14 |
| 6,185,459 B1 | 2/2001 | Mehra et al. ................. 607/14 |
| 6,477,420 B1 | 11/2002 | Struble et al. ................ 607/14 |
| 6,813,516 B1 * | 11/2004 | Ujhelyi et al. ................. 607/4 |
| 6,829,504 B1 * | 12/2004 | Chen et al. .................... 607/4 |
| 2002/0099414 A1 | 7/2002 | Evers et al. .................. 607/14 |

FOREIGN PATENT DOCUMENTS

WO    WO 03/063961    8/2003

* cited by examiner

*Primary Examiner*—Robert E. Pezzuto
*Assistant Examiner*—Tammie K. Heller
(74) *Attorney, Agent, or Firm*—Michael C. Soldner; Girma Wolde-Michael

(57) ABSTRACT

An implantable medical device is directed to techniques for applying overdrive pacing to one or both atria following termination of an AF episode, to prevent a recurrent AF episode. The implantable medical device such as a pacemaker applies overdrive pacing according to overdrive pacing parameters, and sets the parameters as a function of the response of the patient to overdrive pacing. The parameters may be adjusted upward or downward, so that overdrive pacing may be applied effectively but not over-applied.

23 Claims, 5 Drawing Sheets

ADDRESSING RECURRENT ATRIAL FIBRILLATION

TECHNICAL FIELD

The invention generally relates to implantable medical devices (IMD's) such as pacemakers for detecting and treating tachyarrhythmias, and more particularly to techniques employed by IMD's for monitoring and treating recurrent atrial fibrillation.

BACKGROUND

Some heart patients experience episodes of atrial tachyarrhythmia, including atrial fibrillation (AF). Although AF episodes may not be immediately life-threatening, AF episodes may be associated with extreme symptoms, a reduced quality of life, and a reduced cardiac output.

For heart patients having a multi-chamber pacemaker, AF episodes present an additional problem, in that the pacemaker may coordinate ventricular pacing with atrial activity. When an AF episode begins, it is undesirable for ventricular pacing to be timed according to atrial activity. Accordingly, some pacemakers are equipped with "mode switching" capability. The principal purpose of mode switching is to prevent the pacing system from delivering ventricular paces that track atrial activity when the atrium experiences an episode of atrial tachycardia. When the atrial rate is normal, the pacemaker assumes a tracking mode, such as DDD/DDDR, in which ventricular pacing tracks atrial activity. When an AF episode occurs, however, the pacemaker switches to a non-tracking mode, such as DDIR, and paces the ventricle independently of atrial activity.

When an AF episode occurs, the pacemaker or another medical device may apply therapy to terminate the AF episode. Therapy may comprise application of a shock or a drug. Another therapy for atrial tachycardia is overdrive pacing, in which the pacemaker paces one or both atria at a rate faster than their intrinsic rhythm. Overdrive pacing is often effective in disrupting circus arrhythmia and terminating an AF episode. An AF episode may also terminate spontaneously.

It has been observed that a second AF episode may occur within seconds or minutes after the termination of the first AF episode. Although a recurrent AF episode does not always follow the termination of a preceding AF episode, it has been demonstrated clinically that a patient may have an increased risk of a recurrent AF episode shortly after an AF episode has terminated. The phenomenon is called recurrent atrial fibrillation.

SUMMARY

In general, the invention is directed to techniques that apply overdrive pacing to one or both atria following termination of an AF episode, in an effort to prevent a recurrent AF episode. In particular, the invention is directed to techniques for setting or adjusting overdrive pacing parameters to prevent a recurrent AF episode following termination of an AF episode. Overdrive pacing parameters may include the rate and duration of overdrive pacing. Overdrive pacing parameters may also include other parameters, such as the duration of the waiting period between AF episode termination and the onset of overdrive pacing.

Overdrive pacing therapy, in addition to being effective at terminating an AF episode, may be effective at preventing a recurrent AF episode from developing. It is generally not a good practice to engage in overdrive pacing for long durations to prevent AF from occurring, however, because long duration overdrive pacing may be unpleasant for the patient and may drain the power supply for the pacemaker. Similarly, overdrive pacing at a high pacing rate may be unpleasant for the patient. Accordingly, it is generally better for the patient to apply overdrive pacing for a duration when the therapy has a good chance of preventing a recurrent AF episode, but no longer, and to apply overdrive pacing at a rate that is just high enough to prevent an recurrent AF episode, but no higher.

The techniques of the invention may include collecting information about the response of the patient to overdrive pacing. The techniques may further comprise setting overdrive pacing parameters as a function of the response of the patient. When the techniques are applied by a pacemaker, for example, the pacemaker monitors episodes of AF and episodes of recurrent AF, and evaluates whether the overdrive pacing parameters are effective at preventing episodes of recurrent AF. The pacemaker may adjust the parameters upward or downward, adapting the overdrive pacing parameters for the benefit of the patient.

The techniques of the invention may be applied by a pacemaker with mode-switching capability. A pacemaker with mode-switching capability may switch modes following detection of an AF episode or a high atrial rate to pace the ventricles at a rate independent of atrial activity, and may apply therapy such as a shock or overdrive pacing to terminate the AF episode. Because of the possibility of recurrent atrial fibrillation, it may not be beneficial for the pacemaker to resume a tracking mode immediately following termination of an AF episode.

Some of the techniques of the invention, however, may be applied with or without a mode-switching operation. In other words, some of the techniques of the invention may be applied by a pacemaker that is configured to detect an AF episode and to detect termination of the AF episode, whether or not the pacemaker switches modes. The pacemaker may set or adjust overdrive pacing parameters to prevent a recurrent AF episode even if the pacemaker has not switched pacing modes.

In one embodiment, the invention is directed to a method comprising applying overdrive pacing therapy to an atrium according to an overdrive pacing parameter following an episode of atrial fibrillation, monitoring for an episode of recurrent atrial fibrillation and setting the overdrive pacing parameter as a function of the monitoring. Examples of overdrive pacing parameters include an overdrive pacing rate, an overdrive pacing duration, and a duration of a waiting period preceding the overdrive pacing duration.

Detection of an episode of recurrent atrial fibrillation may affect how the overdrive pacing parameter is set. A parameter such as the overdrive pacing rate may be increased when an episode of recurrent atrial fibrillation is detected. The failure to detect an episode of recurrent atrial fibrillation, however, may also affect how the overdrive pacing parameter is set. The overdrive pacing rate, for example, may be decreased when few or no episodes of recurrent atrial fibrillation are detected.

In some embodiments of the invention, threshold-driven techniques may be employed to set overdrive pacing parameters. One embodiment is directed to a method comprising monitoring for episodes of atrial fibrillation in an evaluation period and computing a measure of episodes of detected atrial fibrillation in the evaluation period that are followed by detected recurrent episodes of atrial fibrillation. The method also includes comparing the measure to a threshold and setting an overdrive pacing parameter as a function of the comparison.

In a further embodiment, the invention is directed to an implantable medical device comprising at least one electrode disposed proximate to an atrium of a heart, and a processor for controlling a pulse generator to deliver overdrive pacing therapy to the atrium via the electrode according to an overdrive pacing parameter following an episode of atrial fibrillation. The processor also monitors for a recurrent episode of atrial fibrillation, and sets the overdrive pacing parameter as a function of the monitoring.

In an additional embodiment, the device is directed to a method that includes detecting a fibrillation of an atrium of a heart, delivering a shock therapy to the atrium and immediately thereafter applying an overdrive pacing therapy to the atrium. The method may also include monitoring for an episode of recurrent atrial fibrillation and setting an overdrive pacing parameter as a function of the monitoring.

The invention may offer many advantages, such as the automatic adaptability of overdrive pacing parameters to the particular needs of the patient. The overdrive pacing rate and overdrive pacing duration, for example, may be set to levels that are effective in preventing recurrent AF episodes. The techniques of the invention also keep overdrive pacing rate and overdrive pacing duration from becoming unnecessarily high.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
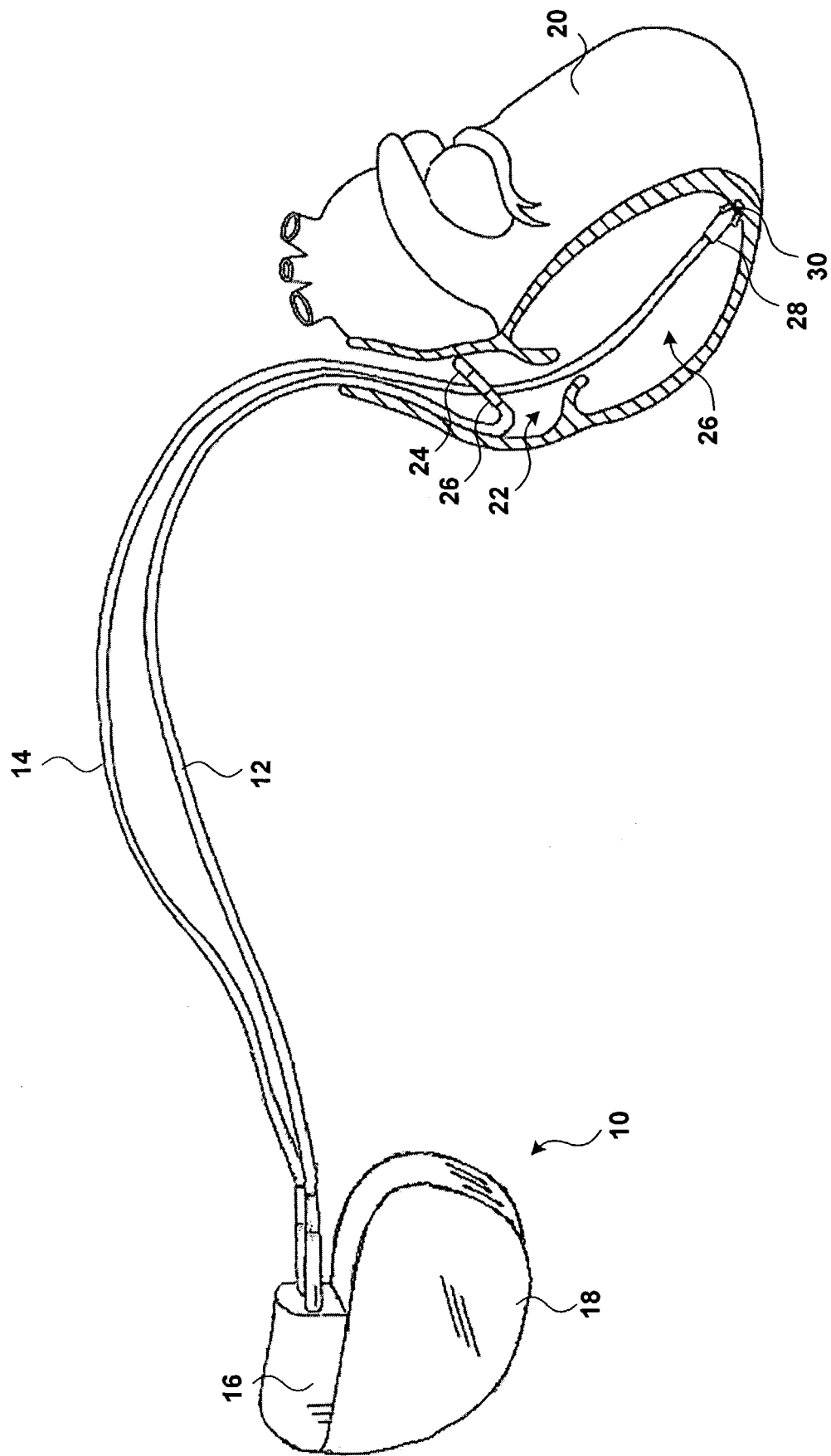
FIG. 1 is a schematic view of an exemplary implantable medical device that may practice the invention, with a heart.

FIG. 1 is a schematic view of one embodiment of an implantable medical device ("IMD") 10 that may practice the techniques of the invention. For example, IMD 10 may be configured to apply overdrive pacing to one or both atria following termination of an AF episode, in an effort to prevent a recurrent AF episode. In particular, IMD 10 may set or adjust overdrive pacing parameters to prevent a recurrent AF episode following termination of an AF episode. IMD 10 is a pacemaker comprising pacing and sensing leads 12 and 14 attached to connector module 16 of hermetically sealed enclosure 18 and implanted near human or mammalian heart 20. Pacing and sensing leads 12 and 14 sense electrical signals attendant to the depolarization and repolarization of the heart 20, and further provide pacing pulses for causing depolarization of cardiac tissue in the vicinity of the distal ends of the leads.

Atrial pacing and sensing lead 12 extends from connector module 16 to the right atrium 22 of heart 20. Atrial electrodes 24 and 26 are disposed in right atrium 22 at the distal end of atrial lead 12. Ventricular pacing and sensing lead 14 extends from connector module 16 to the right ventricle 26 of heart 20. Ventricular electrodes 28 and 30 are disposed in right ventricle 26 at the distal end of ventricular lead 14. The electrodes disposed on the distal ends of leads 12 or 14 may be unipolar or bipolar electrodes.

IMD 10 may pace ventricle 26 with electrodes 28 and 30. IMD 10 may coordinate ventricular pacing with atrial activity sensed via atrial electrodes 24 and 26. Atrial electrodes 24 and 26 may also be employed to sense an atrial tachyarrhythmia such as AF, and to administer therapy, such as overdrive pacing. IMD 10 may be capable of switching pacing modes upon detection of atrial tachyarrhythmia via atrial electrodes 24 and 26.

Overdrive pacing administered via atrial electrodes 24 and 26 may terminate an AF episode in progress, or may prevent an AF episode from recurring. The invention is directed to setting the overdrive pacing parameters that will give IMD 10 a good chance to prevent a recurrent AF episode with overdrive pacing therapy. In particular, IMD 10 may regulate the rate and duration of overdrive pacing and may regulate other facets of overdrive pacing as well.

Figure 2:
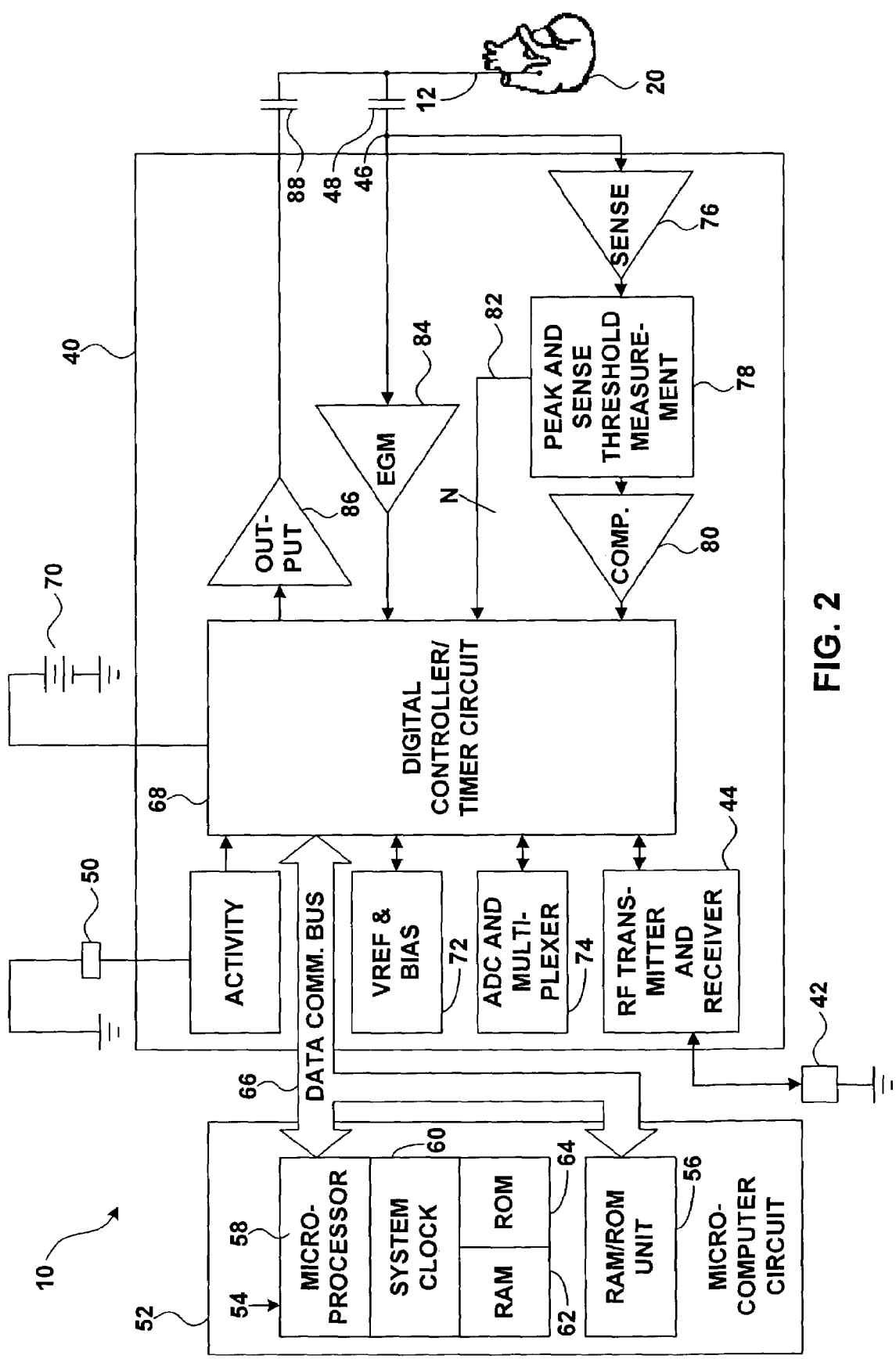
FIG. 2 is a block diagram illustrating the constituent components of an implantable medical device such as the implantable medical device in FIG. 1.

FIG. 2 shows a block diagram illustrating the constituent components of an exemplary IMD 10 in accordance with one embodiment of the invention, in which IMD 10 is a pacemaker having a microprocessor-based architecture. IMD 10 is programmable and may be programmed with an external programming unit (not shown in the figures).

The programmer may provide a series of encoded signals to IMD 10 via wireless telemetry. An input/output circuit 40 may be coupled to an antenna 42 to permit uplink/downlink telemetry through an RF transmitter and receiver telemetry unit 44. In addition to transmitting or receiving programming instructions, telemetry unit 44 may transmit or receive information. Transmitted and received information may include, for example, instructions that cause a processor (such as microprocessor 58, described below) to practice the techniques of the invention. Transmitted and received information may also include default overdrive pacing parameters, or one or more overdrive pacing thresholds as described below, or historical data concerning AF episodes collected by IMD 10. Any of a number of programming and telemetry methodologies may be employed to transmit information to and receive information from IMD 10.

Atrial lead 12 and ventricular lead 14 (not shown in FIG. 2) are coupled to input/output circuit 40. For simplicity, IMD 10 in FIG. 2 is shown with atrial lead 12 connected thereto, but similar circuitry and connections not explicitly shown in FIG. 2 may apply to ventricular lead 14. Lead 12 is coupled to node 46 in IMD 10 through input capacitor 48. Input/output circuit 40 may also deliver pacing stimuli to the atrium as will be described in more detail below.

Input/output circuit 40 may further receive input from an activity sensor or accelerometer 50, such as a piezoceramic accelerometer bonded to a hybrid circuit located inside enclosure 18 (shown in FIG. 1). Activity sensor 50 typically (although not necessarily) provides a sensor output that varies as a function of a measured parameter relating to a patient's metabolic requirements.

IMD 10 includes a microcomputer circuit 52. Microcomputer circuit 52 stores and executes software-implemented algorithms for detecting and responding to arrhythmias such as AF. In some embodiments of the invention, IMD 10 may be programmed to operate in various rate-responsive or non-rate-responsive modes. In addition, microcomputer circuit 52 may store and execute software-implemented algorithms for managing overdrive pacing parameters according to the techniques of the invention, and for controlling delivery of overdrive pacing therapy according to the overdrive pacing parameters.

Microcomputer circuit 52 may include an on-board circuit 54 and off-board circuit 56. On-board circuit 54 includes microprocessor 58, system clock circuit 60 and on-board random-access memory (RAM) 62 and read-only memory (ROM) 64. Off-board circuit 56 comprises a RAM/ROM unit. On-board circuit 54 and off-board circuit 56 are each coupled by a data communication bus 66 to digital controller/timer circuit 68. Microcomputer circuit 52 may comprise a custom integrated circuit device augmented by standard RAM/ROM components. Memory 56, 62 or 64 may store overdrive pacing parameters, and may store data pertaining to the evaluation and efficacy of overdrive pacing therapy, as will be described below.

Electrical components shown in FIG. 2 are powered by an implantable battery power source 70. For the sake of clarity, the coupling of battery power source 70 to the various components of IMD 10 is not shown in the FIG. 2. VREF and bias circuit 72 generates stable voltage reference and bias currents for analog circuits included in input/output circuit 40. Analog-to-digital converter (ADC) and multiplexer unit 74 digitizes analog signals and voltages for digital processing.

Operating commands for controlling the timing of electrical stimulations delivered to heart 20 by IMD 10 are coupled from microprocessor 58 via data bus 66 to digital controller/timer circuit 68, where digital timers and counters establish the various refractory, blanking and other timing windows used in the detection of cardiac activity and the delivery of electrical stimulations.

Sensing circuitry coupled to digital controller/timer circuit 68 detects cardiac activity. Cardiac signals detected via lead 12 are processed by sensing circuitry, which includes sense amplifier 76, peak sense and threshold measurement unit 78 and comparator/threshold detector 80. In general, sense amplifier 76, peak sense and threshold measurement unit 78 and comparator/threshold detector 80 cooperate to sense the occurrence and timing of cardiac events such as atrial activations. Sense amplifier 76 amplifies sensed electrical cardiac signals and provides an amplified signal to peak sense and threshold measurement unit 78, which in turn provides an indication of peak sensed voltages and measured sense amplifier threshold voltages on multiple conductor signal path 82 to digital controller/timer circuit 68. An amplified sense amplifier signal is also provided to comparator/threshold detector 80.

Cardiac signals detected via lead 12 may also be received by electrogram (EGM) amplifier 84. In general, the electrogram signal supplied by EGM amplifier 84 preserves the morphology of the cardiac signal. Digital controller/timer circuit 68 may process the electrogram signal supplied by EGM amplifier 84, and may transmit the electrogram signal to an external programmer for observation and analysis by a physician.

Output pulse generator 86 provides amplified pacing stimuli to heart 20 through coupling capacitor 88 in response to a pacing trigger signal provided by digital controller/timer circuit 68. The conditions that trigger generation of a pacing trigger signal may vary from patient to patient, and the conditions that may trigger generation of an atrial pacing trigger signal need not be the same as the conditions that trigger generation of a ventricular pacing trigger signal. In an embodiment of the invention, digital controller/timer circuit 68 generates atrial pacing trigger signals that cause overdrive pacing of the atrium to terminate an AF episode or to prevent a recurrent AF episode from occurring.

The invention is not limited to application with IMD 10 as depicted in FIGS. 1 and 2. The techniques of the invention may be practiced by, for example, single-chamber pacemakers, or triple- or quadruple-chamber pacemakers. The invention may be practiced by devices that provide a variety of pacing, cardioversion and defibrillation therapies.

Devices that perform overdrive pacing of the atrium supply pacing stimuli to the atrium at a rate, called the "overdrive rate." The overdrive rate may be expressed as the number of paces supplied per unit time during overdrive pacing. In addition, devices that perform overdrive pacing of the atrium supply pacing stimuli at the overdrive rate for a duration of time, called the "overdrive duration." The overdrive rate and overdrive duration are two significant overdrive pacing parameters, but not the only parameters pertaining to overdrive pacing. Other overdrive pacing parameters will be described below.

Figure 3:
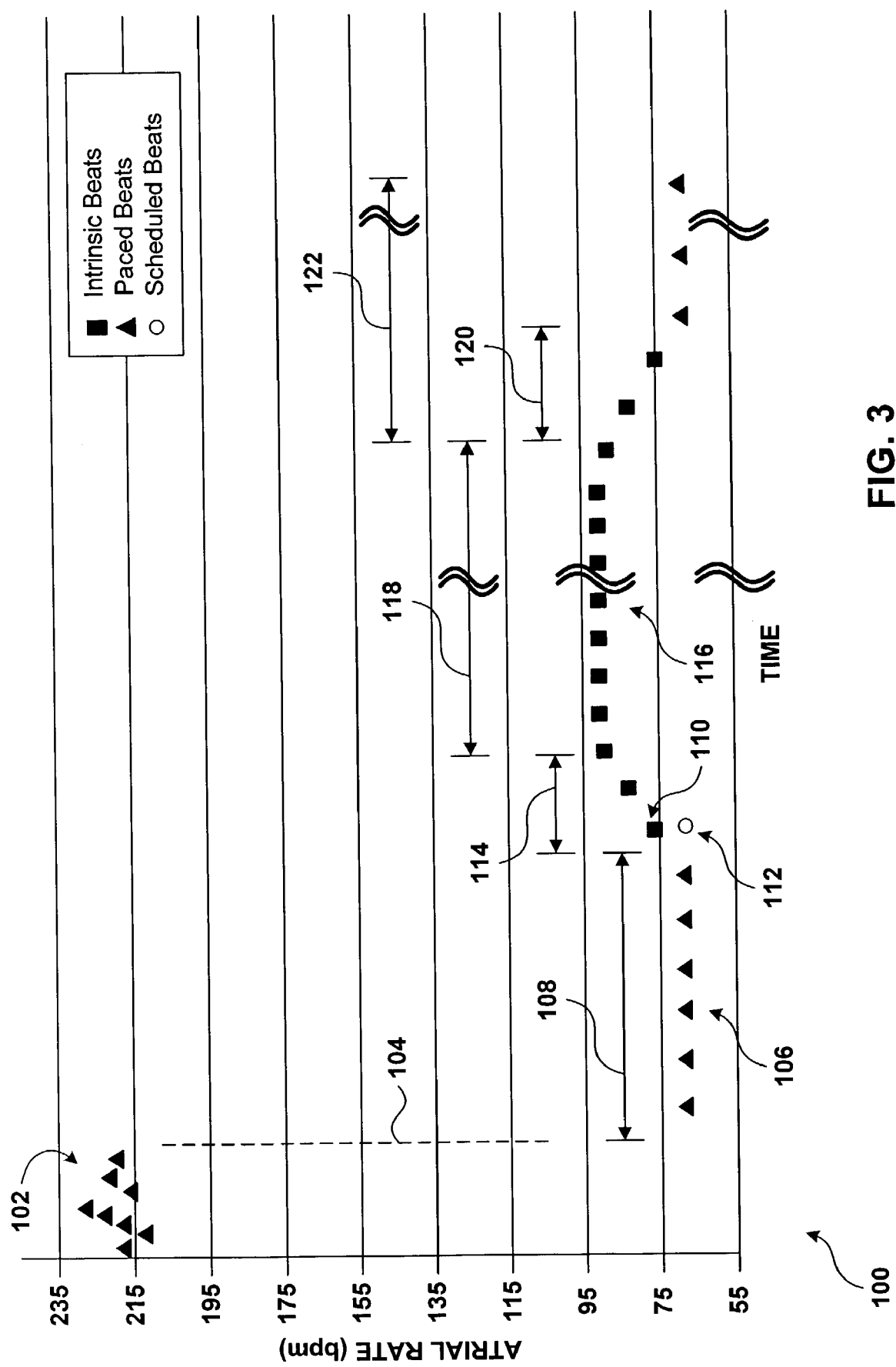
FIG. 3 is a timing diagram illustrating some of the overdrive pacing parameters that may be set according to the techniques of the invention.

FIG. 3 is a timing diagram illustrating several overdrive pacing parameters and management of the parameters according to the invention. The timing diagram illustrates intrinsic atrial beats (represented as triangles) and paced atrial beats (represented as squares) on a graph 100. The horizontal axis of graph 100 represents time and the vertical axis represents the atrial rate in beats (intrinsic or paced) per minute.

The left side of graph 100 shows an AF episode 102, characterized by a collection of rapid intrinsic beats. At some point, denoted by reference line 104, the AF episode terminates. Termination may have been spontaneous, or termination may have been in response to therapy such as administration of a medication, administration of an electrical stimulation, or application of overdrive pacing. Following termination 104 of the AF episode, the patient may exhibit a normal sinus rhythm 106.

In some embodiments of the invention, a pacemaker detects the termination of the AF episode in a waiting period 108 before applying overdrive pacing therapy. The pacemaker may employ any algorithm for sensing termination of an AF episode. The pacemaker may sense six normal sinus rhythm beats, for example, to confirm that the AF episode has terminated. In other embodiments of the invention, the pacemaker does not employ waiting period 108. The pacemaker may, for example, deliver a shock intended to terminate the AF episode, and begin overdrive pacing immediately after delivering the shock, without a waiting period 108.

Following termination of an AF episode, the patient is at risk of experiencing a recurrent AF episode. The term "recurrent" is used herein broadly, and is not limited to a particular time period or number of beats. For example, one physician may deem that an atrial fibrillation episode is "recurrent" when the episode follows within a minute of an earlier terminated episode of atrial fibrillation. Another physician may deem that an atrial fibrillation episode is "recurrent" when the episode follows within three hundred beats of an earlier terminated episode. A third physician may use "recurrent" to refer to an atrial fibrillation episode that follows within ten minutes or six hundred beats of an earlier terminated episode, whichever is longer. The invention encompasses all such usages of the word "recurrent."

When the patient is at risk of experiencing recurrent AF episode, a pacemaker may begin overdrive pacing by delivering a paced beat 110 prior to a scheduled beat 112, thereby driving the atrium to beat faster than the intrinsic rate of the atrium. In a typical application, the pacemaker does not abruptly switch to the overdrive pacing rate. Rather, the pacemaker may ramp up to the overdrive pacing rate in a transition period 114, i.e., incrementally increase the pacing rate up to the overdrive pacing rate. Transition period 114 is not required, however, and the pacemaker may abruptly begin pacing at the overdrive pacing rate.

The pacemaker paces one or both atria at an overdrive pacing rate 116 for an overdrive pacing duration 118. Graph 100 shows an example overdrive pacing rate of about 90 beats (i.e., paces) per minute. At the end of overdrive pacing duration 118, the pacemaker may ramp down from the overdrive pacing rate in a transition period 120. The pacemaker may continue to monitor for AF in a monitoring period 122 that follows overdrive pacing. The monitoring period may extend for any period of time.

Even though a pacemaker may administer overdrive pacing therapy following termination of an AF episode, another AF episode may nevertheless recur. The recurrence of an AF episode during overdrive pacing duration 118 may suggest that the overdrive pacing rate is too slow. The recurrence of an AF episode during monitoring period 122 may suggest that overdrive pacing duration 118 is too brief. The invention is directed to techniques by which a pacemaker adjusts overdrive pacing parameters, such as the overdrive pacing rate and overdrive pacing duration, to prevent early recurrence of AF episodes.

Figure 4:
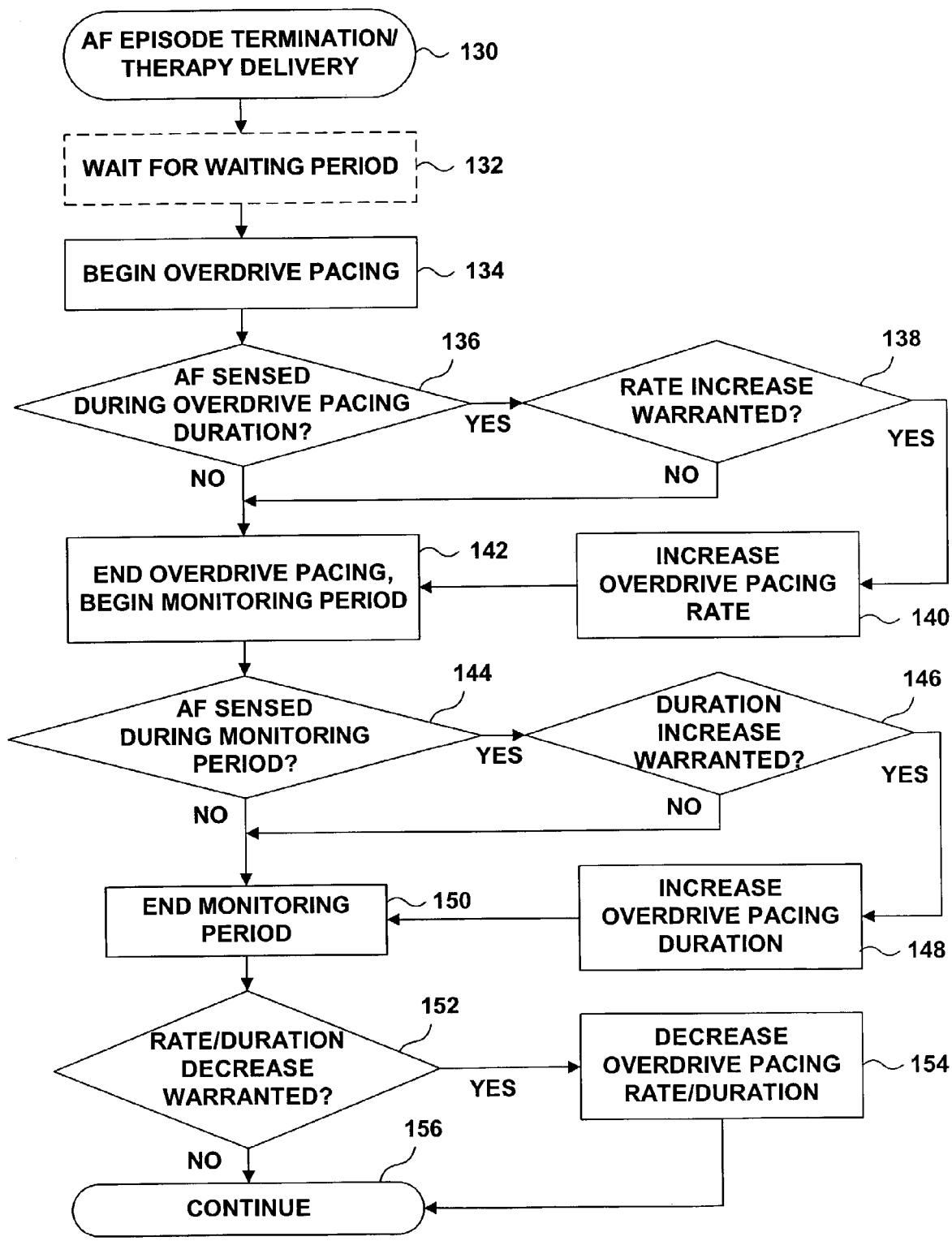
FIG. 4 is a flow diagram illustrating techniques for setting overdrive pacing parameters.

FIG. 4 is flow diagram illustrating techniques used by a pacemaker to set the overdrive pacing rate, or the overdrive pacing duration, or both, following termination of an AF episode or delivery of AF therapy (130). As used herein, "setting" an overdrive pacing parameter is defined broadly, and includes selecting a new value for a parameter and adjusting a previous value of the parameter.

After termination of an AF episode (130), the pacemaker may undergo a waiting period before beginning overdrive pacing (134). The waiting period (132) is, however, not essential to the invention. In some circumstances, the pacemaker uses a waiting period to detect that the AF episode has terminated. In some embodiments of the invention, however, the pacemaker may begin overdrive pacing (134) without waiting for detection of episode termination. The pacemaker may, for example, deliver shock therapy (130) intended to terminate the AF episode, and begin overdrive pacing (134) immediately after delivering the therapy.

Overdrive pacing begins at an overdrive pacing rate, and continues for an overdrive pacing duration (134) The pacemaker may ramp the pacing rate up to the overdrive pacing rate as shown in FIG. 3. When the pacemaker senses an AF episode during the overdrive pacing duration (136), the recurrence of AF is evidence that the overdrive pacing rate is too slow.

In some embodiments of the invention, the pacemaker may be programmed to recognize that a single observed AF episode during the overdrive pacing duration warrants an increase in the overdrive pacing rate. In other embodiments of the invention, however, a pacemaker may be programmed to not to increase in the overdrive pacing rate based upon a single episode. In these embodiments, a single recurrence of AF may be evidence that the overdrive pacing rate is too slow, but insufficient by itself to warrant a change to the overdrive pacing rate.

Criteria that warrant an increase in the overdrive pacing rate may defined in any number of ways. One pacemaker, for example, may be programmed to increase the overdrive pacing rate when recurrent AF episodes have been detected following two consecutive terminated AF episodes. Another pacemaker may be programmed to increase the overdrive pacing rate using a threshold-driven technique, as will be described below. The invention encompasses all criteria for deciding whether an increase in the overdrive pacing rate is warranted.

When an increase in the overdrive pacing rate is warranted (138), the pacemaker increases the overdrive pacing rate (140). The amount of the increase may be a pre-determined value, such as five beats (i.e., paces) per minute. The amount of the increase may also be defined in other ways as well, such as a five percent increase above the current overdrive pacing rate.

The increase in the overdrive pacing rate may take effect at any time. In a typical application of the invention, the increase in the overdrive pacing rate takes effect following termination of the AF episode in progress. When the AF episode in progress terminates (130), overdrive pacing may begin (134) with the increased overdrive pacing rate.

Upon the expiration of the overdrive pacing duration, overdrive pacing ends and a monitoring period begins (142). The pacemaker may ramp the pacing rate down from the overdrive pacing rate as shown in FIG. 3. If the pacemaker has previously switched from a tracking mode to a non-tracking mode, the pacemaker may switch back to a tracking mode upon the expiration of overdrive pacing duration, or the pacemaker may switch back to a tracking mode at another time.

When an AF episode is detected during the monitoring period (144), the recurrence of AF in the monitoring period is evidence that the overdrive pacing duration is too brief. The pacemaker may determine whether the evidence of an AF episode in the monitoring period warrants an increase in the overdrive pacing duration (146). As with increases to the overdrive pacing rate, a single observed AF episode during the monitoring period may or may not warrant an increase in the overdrive pacing duration. A pacemaker may be programmed, for example, to increase the overdrive pacing duration using a threshold-driven technique, as will be described below, or using other criteria. The invention encompasses all criteria for deciding whether an increase in the overdrive pacing duration is warranted.

When an increase in the overdrive pacing duration is warranted (146), the pacemaker increases the overdrive pacing duration (148). The amount of the increase may be a pre-determined value, such as five seconds, or a percentage increase over the current overdrive pacing duration, for example.

The increase in the overdrive pacing duration may take effect at any time, but typically the increase in the overdrive pacing duration takes effect following termination of the recurrent AF episode.

The physician for the patient may set default values for overdrive pacing parameters such as the overdrive pacing rate and the overdrive pacing duration. Following episodes of AF, the pacemaker may adapt the overdrive pacing parameters so as to address recurrent AF more effectively. In the event no AF episodes are detected during the overdrive pacing duration and during the monitoring period, then overdrive pacing may be considered to be successful. When several AF episodes terminate and few or no recurrent AF episodes take place, this result is evidence that the overdrive pacing is effective in preventing recurrence of AF episodes.

Even if no recurrent AF episodes are detected, however, it is not necessarily true that the overdrive pacing rate and overdrive pacing duration are best for the patient. It is possible, for example, that the physician may have set the default values for these parameters higher than necessary. It is also possible that, even though the overdrive pacing rate and the overdrive pacing duration may have been increased according to the techniques described above, the parameters may have been increased by too large an amount, and that lower values for the parameters will be equally effective in preventing recurrent AF. In general, overdrive pacing should be used when the patient is at risk of experiencing a recurrent AF episode, and overdrive pacing should not be used when the risk has passed.

From the standpoint of the patient, it is desirable to use an overdrive pacing rate and an overdrive pacing duration that are high enough to prevent recurrent AF, but no higher. Overdrive pacing can be uncomfortable for the patient, causing symptoms such as loss of sleep and loss of enjoyment of life. In general, the discomfort increases as the overdrive pacing rate and the overdrive pacing duration increase. AF may be uncomfortable as well, so it is desirable to strike a balance in which overdrive pacing is applied to be effective at preventing recurrent AF, but is not over-applied. In addition, providing too much overdrive pacing causes a drain the power supply for the pacemaker.

Accordingly, the techniques depicted in FIG. 4 also allow the pacemaker to decrease the overdrive pacing rate, the overdrive pacing duration, or both. The pacemaker may decrease either parameter following the monitoring period (150). The pacemaker determines whether a decrease in the overdrive pacing rate or overdrive pacing duration is warranted (152). The pacemaker may be programmed to recognize, for example, that a certain number of AF episodes, followed by no recurrent AF episodes in the overdrive pacing duration, warrants a decrease in the overdrive pacing rate.

When warranted, the pacemaker may decrease the overdrive pacing rate or the overdrive pacing duration or both (154). The amount of the decrease need not be the same as the amount of the increases (140, 148). When a later AF episode terminates (130), the overdrive pacing rate or overdrive pacing duration will again be evaluated for efficacy, and may be increased or decreased again. In a typical application, the parameters are set independently. When the pacemaker increases the overdrive pacing rate, for example, the pacemaker may increase the overdrive pacing duration, or decrease the overdrive pacing duration, or keep the overdrive pacing duration unchanged.

In this way, the overdrive pacing rate and the overdrive pacing duration may be increased or decreased. As a result, the overdrive pacing rate and the overdrive pacing duration may adapt to prevent recurrent AF, and to do so without over-application of overdrive pacing therapy.

In one embodiment of the invention, the pacemaker may increase and decrease the overdrive pacing rate and the overdrive pacing duration over time, without settling on a final value for either parameter. In another embodiment of the invention, however, it may be possible to for the parameters to settle at stable values.

Figure 5:
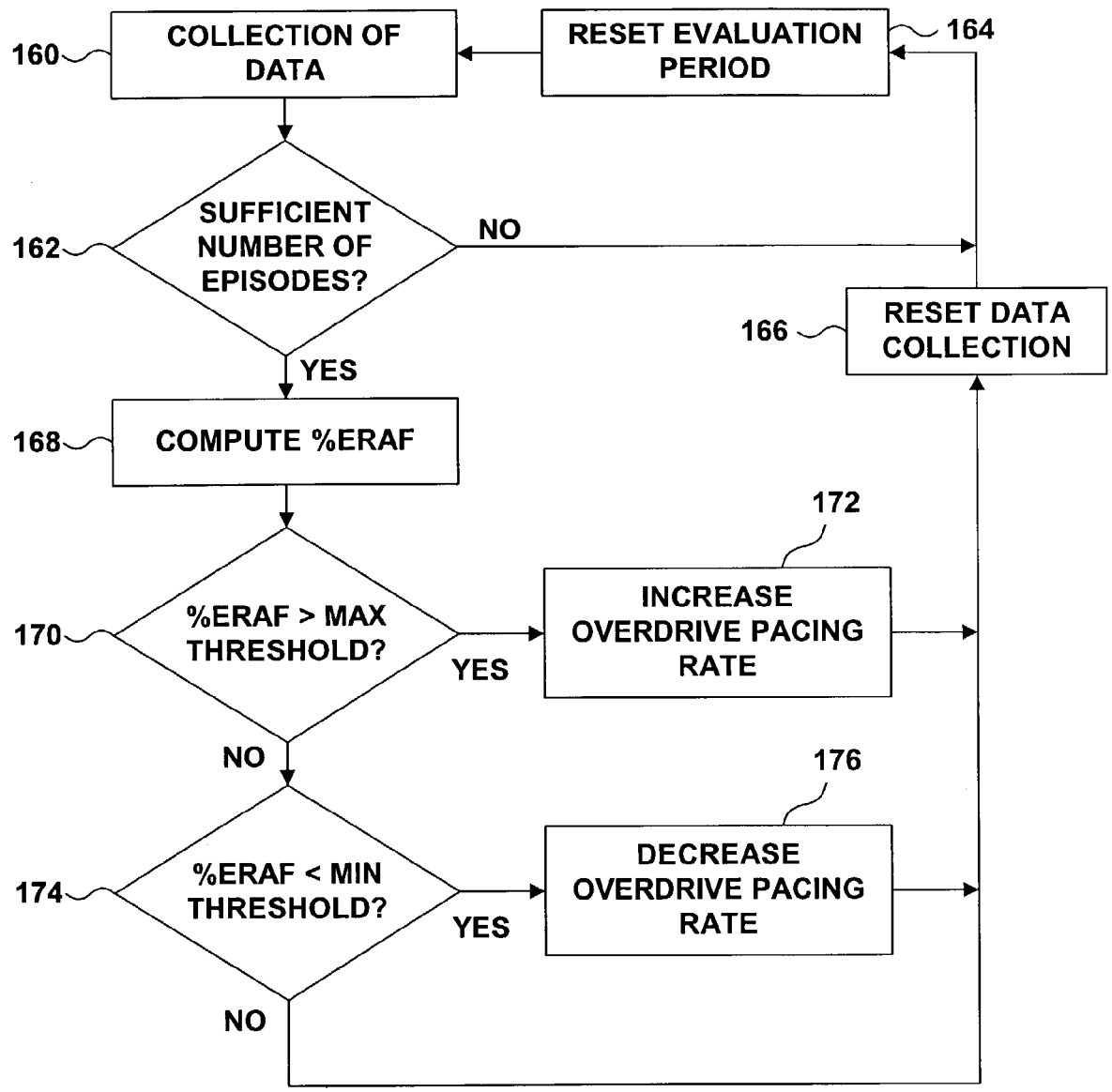
FIG. 5 is a flow diagram illustrating techniques for setting overdrive pacing parameters using thresholds.

FIG. 5 is a flow diagram illustrating a threshold-driven technique for setting overdrive pacing parameters. With this technique, there is a learning period, or "evaluation period," during which the pacemaker collects data about recurrent AF episodes. During the evaluation period, the pacemaker monitors for episodes of atrial fibrillation and monitors for episodes of recurrent atrial fibrillation that follow. After the data are collected, a measure of recurrent AF episodes per terminated AF episodes is computed and compared to a high threshold and a low threshold, and the overdrive pacing parameter may be set as a function of the comparison.

FIG. 5 illustrates the technique with an overdrive pacing rate, but a similar technique may be employed for other overdrive pacing parameters as well. During an evaluation period, the pacemaker collects data (160) pertinent to the overdrive pacing rate. An evaluation period may be specified, for example, as a number of days, such as fourteen days. An evaluation period may also be specified as a function of a number of episodes, such as a number of AF episodes and recurrent AF episodes.

During the evaluation period, the pacemaker records the number of AF episodes that have been detected. Following termination of these AF episodes, the pacemaker may have applied overdrive pacing therapy. The pacemaker further monitors for recurrent atrial fibrillation episodes. The pacemaker records the number of detected episodes of recurrent atrial fibrillation.

At the expiration of the evaluation period, it is possible that there may have been too few detected episodes of AF to be statistically significant (162), and in that event, the overdrive pacing rate may remain unchanged and the pacemaker may reset the evaluation period (164). Data collected during the evaluation period may be discarded (166) or retained. In the example of FIG. 5, the data are retained, and data collected in the new evaluation period are added to previously collected data.

When the pacemaker has collected enough data (162), the pacemaker computes a measure of the AF episodes in the evaluation period that were followed by recurrent episodes (168). The recurrent episodes may have recurred during the overdrive pacing duration. This computation may be expressed, for example, as a percentage of recurrent episodes per total AF episodes (denoted in FIG. 5 as % ERAF).

The measure is compared to a maximum threshold and a minimum threshold. When % ERAF is greater than the maximum threshold (170), then the overdrive pacing rate may be too low. Accordingly, the pacemaker increases the overdrive pacing rate (172). Similarly, when % ERAF is below than the minimum threshold (174), then the overdrive pacing rate may be too high, and the pacemaker decreases the overdrive pacing rate (176). The pacemaker may reset data collection (166) and reset the evaluation period (164) and begin collecting new data under the newly set overdrive pacing parameters.

As with the techniques described above in connection with FIG. 4, the amount of the increase or decrease may be a pre-determined value, or a percentage of the current overdrive pacing rate, or some other increase or decrease. The amount of a decrease need not be the same as the amount of an increase.

The physician for the patient may set the amount of increase or decrease, and may set the thresholds that govern whether an increase or decrease takes place. The physician may also set maximum or minimum values for the parameters. For example, the physician may program the pacemaker such that the overdrive pacing rate will never exceed 130 beats per minute and will not be lower than 70 beats per minute.

The computation of % ERAF is an illustrative example of a measure that may be compared to a maximum threshold and a minimum threshold, but it is not the only possible quantity that may be used. In some embodiments of the invention, different computations may be performed. The collected data may be analyzed by, for example, preparing a histogram or data distribution as a function of the time elapsed between the termination of the AF episode and the recurrent AF episode. % ERAF may therefore be embodied as a data distribution, rather than as a single value. The thresholds likewise may be sets of threshold values, rather than one maximum or minimum value.

Furthermore, the techniques shown in FIG. 5 are not limited to setting the overdrive pacing rate. A pacemaker may apply similar data collection and threshold comparison techniques for setting the overdrive pacing duration. In particular, a pacemaker may collect data during an evaluation period about the number of episodes that occur within a monitoring period following the overdrive pacing duration. The pacemaker may calculate a percentage of recurrent AF episodes that occur in the monitoring period, and may compare the percentage to high and low thresholds. When the percentage is above the high threshold, the pacemaker may increase the overdrive pacing duration, and when the percentage is below the low threshold, the pacemaker may decrease the overdrive pacing duration.

Moreover, the techniques shown in FIGS. 4 and 5 may be applied to parameters other than or in addition to the overdrive pacing rate and the overdrive pacing duration. Other overdrive pacing parameters may include the duration of the waiting period, for example. Setting the waiting period may affect how quickly overdrive pacing therapy begins following termination of an AF episode. The techniques shown in FIGS. 4 and 5 may also be applied to discontinue or change the duration of a transition period such as ramping up transition period 114. The invention may offer several advantages. A pacemaker may set overdrive pacing parameters that adapt to the particular needs of the patient. The pacemaker works to provide overdrive pacing at a rate and duration that are effective in preventing recurrent AF episodes, while keeping the rate and duration from becoming unnecessarily high. When a patient needs adjustments to the overdrive pacing parameters, the pacemaker automatically sets the parameters to effective levels without intervention or reprogramming by the physician.

In addition, the pacemaker continues to monitor whether the patient could be well served by less therapy. By reducing the overdrive pacing rate or the overdrive pacing duration when warranted, the pacemaker may provide an effective overdrive pacing therapy that is as effective and more comfortable for the patient. In addition, the pacemaker may set the overdrive pacing parameters independently of one another.

Various embodiments of the invention have been described. These embodiments are illustrative of the practice of the invention. Various modifications may be made without departing from the scope of the claims. For example, the invention is not limited to a particular physical construction of a pacemaker or to any particular lead placement. Nor is the invention limited to use with any specified arrhythmia detection or therapy algorithms. Any implantable device capable of providing overdrive pacing therapy may practice embodiments of the invention.

Moreover, the invention encompasses techniques that define overdrive pacing parameters in different ways. For example, the invention encompasses embodiments in which the "overdrive pacing rate" is defined in terms of an "overdrive pacing interval," i.e., a time interval between successive paces. The invention encompasses embodiments in which the "overdrive pacing duration" is defined to include the time interval during which the pacemaker paces an atrium at the overdrive pacing rate, and the invention also encompasses embodiments in which the "overdrive pacing duration" is defined to include one or more transition periods, such as transition periods 114 and 120 in FIG. 3. In addition, FIG. 3 depicts transition period 120 as included in monitoring period 122, but the invention encompasses embodiments that do not include a transition period in the monitoring period.

The invention may be embodied as a device that carries out the techniques described above. The invention may also be embodied as a computer-readable medium comprising instructions that cause a processor, such as microprocessor 58 or digital controller/timer circuit 68 shown in FIG. 2, to practice the techniques. A "computer-readable medium" includes but is not limited to read-only memory, Flash memory and a magnetic or optical storage medium. The medium may comprise instructions for causing a programmable processor to set one or more overdrive pacing parameters as a function of sensing following an episode of atrial fibrillation. These and other embodiments are within the scope of the following claims.

What is claimed is:

1. A method comprising:
   controlling a pulse generator to deliver overdrive pacing therapy to an atrium via an electrode disposed proximate to the atrium of a heart according to an overdrive pacing parameter following an episode of atrial fibrillation;
   monitoring for an episode of recurrent atrial fibrillation;
   receiving a threshold via a telemetry unit;
   computing a measure of episodes of atrial fibrillation in an evaluation period that are followed by recurrent episodes of atrial fibrillation;
   comparing the measure to the threshold; and
   setting the overdrive pacing parameter as a function of the comparing.

2. The method of claim 1, wherein the overdrive pacing parameter comprises at least one of an overdrive pacing rate, an overdrive pacing duration, and a waiting period preceding the overdrive pacing duration.

3. The method of claim 1, further comprising detecting a termination of the first episode of atrial fibrillation prior to applying the overdrive pacing therapy.

4. The method of claim 3, further comprising waiting for a waiting period between the termination of the first episode of atrial fibrillation and applying the overdrive pacing therapy.

5. The method of claim 1, further comprising:
   administering a shock therapy to the atrium following a detection of the first episode of atrial fibrillation; and
   applying the overdrive pacing therapy immediately after administering the shock therapy.

6. The method of claim 1, further comprising monitoring for the occurrence of an episode of recurrent atrial fibrillation while applying the overdrive pacing therapy.

7. The method of claim 6, further comprising:
   applying the overdrive pacing therapy at an overdrive pacing rate;
   detecting an episode of recurrent atrial fibrillation while applying the overdrive pacing therapy; and
   increasing the overdrive pacing rate.

8. The method of claim 1, further comprising monitoring for the occurrence of an episode of recurrent atrial fibrillation in a monitoring period after applying the overdrive pacing therapy.

9. The method of claim 8, further comprising:
   applying the overdrive pacing therapy for an overdrive pacing duration;
   detecting an episode of recurrent atrial fibrillation in the monitoring period; and
   increasing the overdrive pacing duration.

10. The method of claim 1, further comprising:
applying the overdrive pacing therapy at an overdrive pacing rate for an overdrive pacing duration; and
decreasing at least one of the overdrive pacing rate and the overdrive pacing duration.

11. A computer-readable medium comprising instructions for causing a programmable processor to:
control a pulse generator to deliver overdrive pacing therapy to an atrium via an electrode disposed proximate to the atrium of the heart according to an overdrive pacing parameter following a first episode of atrial fibrillation;
monitor for an episode of recurrent atrial fibrillation;
receive a threshold via a telemetry unit;
compute a measure of episodes of atrial fibrillation in an evaluation period that are followed by recurrent episodes of atrial fibrillation;
compare the measure to the threshold; and
set the overdrive pacing parameter as a function of the comparing.

12. The medium of claim 11, wherein the overdrive pacing parameter comprises at least one of an overdrive pacing rate, an overdrive pacing duration, and a waiting period preceding the overdrive pacing duration.

13. The medium of claim 11, the instructions further causing the processor to detect a termination of the first episode of atrial fibrillation prior to applying the overdrive pacing therapy.

14. The medium of claim 13, the instructions further causing the processor to wait for a waiting period between the termination of the first episode of atrial fibrillation and applying the overdrive pacing therapy.

15. The medium of claim 11, the instructions further causing the processor to:
administer a shock therapy to the atrium following a detection of the first episode of atrial fibrillation; and
apply the overdrive pacing therapy immediately after administering the shock therapy.

16. The medium of claim 11, the instructions further causing the processor to monitor for the occurrence of an episode of recurrent atrial fibrillation while applying the overdrive pacing therapy.

17. The medium of claim 16, the instructions further causing the processor to:
apply the overdrive pacing therapy at an overdrive pacing rate;
detect an episode of recurrent atrial fibrillation while applying the overdrive pacing therapy; and
increase the overdrive pacing rate.

18. The medium of claim 11, the instructions further causing the processor to monitor for the occurrence of an episode of recurrent atrial fibrillation in a monitoring period after applying the overdrive pacing therapy.

19. The medium of claim 18, the instructions further causing the processor to:
apply the overdrive pacing therapy for an overdrive pacing duration;
detect an episode of recurrent atrial fibrillation in the monitoring period; and
increase the overdrive pacing duration.

20. The medium of claim 11, the instructions further causing the processor to:
apply the overdrive pacing therapy at an overdrive pacing rate for an overdrive pacing duration; and
decrease at least one of the overdrive pacing rate and the overdrive pacing duration.

21. An implantable medical device comprising:
at least one electrode disposed proximate to an atrium of a heart;
a pulse generator coupled to the electrode;
a processor to control the pulse generator to deliver overdrive pacing therapy to the atrium via the electrode according to an overdrive pacing parameter following an episode of atrial fibrillation, monitor for an episode of recurrent atrial fibrillation, and set the overdrive pacing parameter as a function of the monitoring; and
a telemetry unit to receive a threshold, wherein the processor computes a measure of episodes of atrial fibrillation in an evaluation period that are followed by recurrent episodes of atrial fibrillation, compares the measure to a threshold and sets an overdrive pacing parameter as a function of the comparison.

22. The device of claim 21, further comprising sensing circuitry to detect the episode of atrial fibrillation and monitor for the episode of recurrent atrial fibrillation.

23. The device of claim 21, wherein the device operates in a plurality of pacing modes, and wherein the device selects a pacing mode as a function of a detected episode of atrial fibrillation.

* * * * *